United States Patent
Kwun et al.

(10) Patent No.: US 7,019,520 B2
(45) Date of Patent: Mar. 28, 2006

(54) METHOD AND SYSTEM FOR TORSIONAL WAVE INSPECTION OF HEAT EXCHANGER TUBES

(75) Inventors: Hegeon Kwun, San Antonio, TX (US); James F. Crane, San Antonio, TX (US); Sang-Young Kim, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/711,747

(22) Filed: Oct. 1, 2004

(65) Prior Publication Data

US 2005/0104584 A1    May 19, 2005

Related U.S. Application Data

(60) Provisional application No. 60/481,636, filed on Nov. 13, 2003.

(51) Int. Cl.
*G01N 27/82* (2006.01)
*G01M 15/00* (2006.01)
*G01M 13/00* (2006.01)

(52) U.S. Cl. ......................... 324/238; 73/650
(58) Field of Classification Search ................ None
See application file for complete search history.

(56) References Cited

U.S. PATENT DOCUMENTS

| 4,505,323 | A | * | 3/1985 | de la Pintiere et al. ..... 165/11.2 |
| 5,760,306 | A | * | 6/1998 | Wyatt et al. .................. 73/623 |
| 5,892,162 | A | * | 4/1999 | Spinks et al. .............. 73/865.8 |
| 6,707,290 | B1 | * | 3/2004 | Nyce et al. ............ 324/207.13 |

* cited by examiner

*Primary Examiner*—Bot LeDynh
(74) *Attorney, Agent, or Firm*—Taylor Russell & Russell, P.C.

(57) ABSTRACT

The invention provides an improved method and device for inspecting heat exchanger tubes from within the tube inside diameter that overcomes the shortcomings of the prior art. It adapts a guided-wave probe approach that makes use of a torsional wave mode instead of a longitudinal wave node disclosed in the prior art. The torsional wave mode has many advantages over the longitudinal wave mode for detecting defects. When energized by suitable instrumentation, the probe is caused to generate a torsional mode signal that is transmitted to the heat exchanger tube from the waveguide tube. When reflected signals from defects in the heat exchanger tube walls are returned to the inspection opening end of the heat exchanger tube, the reflected defect signals are transmitted to the probe waveguide tube for amplification, detection and characterization of the reflected signal.

20 Claims, 9 Drawing Sheets

METHOD AND SYSTEM FOR TORSIONAL WAVE INSPECTION OF HEAT EXCHANGER TUBES

This application claims the benefit of U.S. Provisional Application No. 60/481,636, filed on Nov. 13, 2003, which is incorporated herein by reference.

BACKGROUND

The invention relates generally to a method and system for inspection of heat exchanger tubes using long-range guided-wave inspection techniques, and more particularly to a method using torsional guided waves for quickly inspecting heat exchanger tubes from the inside diameter of a tube.

Heat exchangers are used extensively in processing plants such as refineries, chemical plants and electric generation facilities, and typically comprise a multiplicity of heat exchanger tubes supported in a fixed position by a tube sheet. Each heat exchanger tube is accessible from one end for inspection and maintenance purposes. The heat exchanger tubes carry a first liquid or gas at a first temperature and are surrounded by a second liquid or gas at a second temperature, whereby heat is transferred from the first liquid or gas to the second liquid or gas, or visa-versa. In order to minimize forced shutdowns of equipment and processes due to heat exchanger failures and associated operating and maintenance costs, heat exchanger tubes are inspected on a regular basis. Since heat exchanger tubes are bundled in close proximity, making it difficult to inspect them from their outer diameter, inspections of heater exchanger tubes are conducted from the inside diameter of the tube. Because of the large number of heat exchanger tubes in a heat exchanger and the high cost of inspection, heat exchanger tubes are generally maintained based on sampled inspection data from a small number of tubes. This current maintenance practice does not result in high reliability of heat exchangers.

There have been a number of past efforts to find solutions for inspecting heat exchanger tubes. Many of these efforts have relied on inducing guided waves in the heat exchanger tube walls and detecting induced guided wave signals reflected from defects in the tube walls. Some of these solutions provided a means for inspecting a long length of tubing from a fixed probe location on the outside diameter of tubes for detection of reflected guided wave signals. The difficulty in accessing the outside diameter of heat exchanger tubes has rendered this approach impracticable. However, these methods have provided recognition that a potential solution for quickly surveying heat exchanger tube integrity, provided that the guided waves could be launched and detected from the inside diameter of the heat exchanger tubes. Because of various shortcomings of solutions disclosed in the prior art, including poor efficiency, poor defect detection capability and mode control difficulties, these solutions have not been widely accepted for practical heat exchanger tube inspections in the field.

There is a need for a nondestructive testing method in processing industries for enhancing reliability and reducing costs by quickly surveying all heat exchanger tubes in a heat exchanger and providing data suitable for determining appropriate subsequent inspection and maintenance actions. A desirable technique is one that can be applied from an inside diameter of a heat exchanger tube, can quickly inspect the entire length of a tube from one end, and requires cleaning only in an area of probe placement.

SUMMARY

The present invention provides a nondestructive testing method for enhancing reliability and reducing costs by quickly surveying all heat exchanger tubes in a heat exchanger and providing data suitable for determining appropriate subsequent inspection and maintenance actions. It provides for inspection of the entire length of all of the tubes from one tube end inside diameter, requiring cleaning of only a probe placement area on each tube.

The disclosed invention provides an improved method and system for inspecting heat exchanger tubes from within the tube inside diameter that overcomes the shortcomings of the prior art. The invention relies on a magnetostrictive transmitter and a tubular waveguide to generate torsional waves in the waveguide that are coupled to the inside of a heat exchanger tube for transmitting the torsional waves into the heat exchanger tube. The torsional waves reflect from defects and irregularities in the heat exchanger tube walls, return to the coupled waveguide and are sensed by the magnetostrictive sensor. It adapts a guided-wave probe approach that makes use of a torsional wave mode instead of a longitudinal wave node disclosed in the prior art. The torsional wave mode has many advantages over the longitudinal wave mode for detecting defects. Among the advantages of the use of torsional wave mode are greatly reduced wave dispersion, easier mode control, reduced interference from other wave modes, immunity to the presence of liquid product, and improved defect detectability. The invented probe generates and detects the torsional waves in a waveguide tube, which is in close contact with the inside diameter of a heat exchanger tube for coupling of torsional waves between the waveguide tube and the heat exchanger tube. The waveguide tube makes use of damping material to minimize reverberation of a guided-wave signal within the waveguide tube. Axial slits near the working waveguide tip end of the waveguide tube allow expansion for providing close contact with the inside wall of a heat exchanger tube for coupling the torsional waves between the heat exchanger tube and the waveguide tube. When energized by suitable instrumentation, the probe is caused to generate a torsional wave signal that is coupled to the heat exchanger tube from the waveguide tube. When reflected signals from defects in the heat exchanger tube walls are returned to the inspection opening end of the heat exchanger tube, the reflected defect signals are coupled to the probe waveguide tube for detection of the reflected signals.

It should be noted that within the context of this specification, the term "sensor" is used to describe a device attached to a waveguide that is capable of transmitting and receiving torsional waves in the waveguide. Furthermore, it is recognized that a transmitting sensor may also be a separate distinct device from a receiving sensor.

An embodiment of the present invention is a method for inspection of heat exchanger tubes using reflected torsional waves comprising the steps of inserting a cylindrical waveguide probe into an open end of a heat exchanger tube, a coupled end of the waveguide probe being located a distance from the open end by at least the distance from the open end to a heat exchanger tube sheet, applying an electronic transmit pulse to a magnetostrictive sensor mounted on the waveguide probe, generating and transmitting a torsional wave pulse in the waveguide probe by the magnetostrictive sensor, coupling the transmitted torsional wave from the waveguide probe to an inside wall of the heat exchanger tube for propagation along the length of the heat exchanger tube, coupling reflected torsional wave signals from defects and a far end of the heat exchanger tube to the waveguide probe, sensing the reflected torsional wave signals by a magnetostrictive sensor, and electronically processing the sensed signals for determining a location and characteristics of the defects in the heat exchanger tube walls. The step of generating a torsional wave pulse and the step of sensing the reflected torsional wave signals may be performed by the same magnetostrictive sensor including an integrated magnetostrictive transmitter and receiver. The step of generating a torsional wave pulse and the step of sensing the reflected torsional wave signals may be performed by separate magnetostrictive sensors including a magnetostrictive transmitter and separate magnetostrictive receiver. The step of generating torsional waves may comprise applying an electric current pulse of a fixed frequency to a coil wound over a ferromagnetic strip of the magnetostrictive sensor cylindrically affixed on the cylindrical waveguide probe. The ferromagnetic strip may be selected from the group consisting of a nickel strip and a strip of material having good magnetostrictive properties. The method may further comprise the step of magnetically polarizing the ferromagnetic strip in a circumferential direction. The step of coupling the torsional waves between the waveguide tube and the heat exchanger tube may comprise expanding the coupled end of the waveguide tube to make intimate contact between the coupled end and the inside diameter of the heat exchanger tube by applying a force from inside the waveguide tube using an expansible device. The method wherein the step of applying an electronic transmit pulse may comprise activating a function generator by an output of a control processor for generating a transmit pulse, connecting the transmit pulse at an output of the function generator to a power amplifier input for amplifying the transmit pulse, and applying the amplified output pulse from the output of the power amplifier to the magnetostrictive sensor, wherein the step of electronically processing the reflected torsional waves may comprise amplifying a signal from the magnetostrictive sensor in a preamplifier, connecting the amplified signal at an output of the preamplifier to an input of an analog-to-digital converter, and connecting an output of the analog-to-digital converter to an input of the control processor, and may further comprise the step of determining locations and characteristics of defects in the heat exchanger tube walls by the control processor using signal characteristics from the analog-to-digital converter output and the time differences between applying the electronic transmit pulse and sensing of the signal characteristics from the analog-to-digital converter output.

Another embodiment of the present invention is a system for inspection of heat exchanger tubes using reflected torsional waves, comprising a cylindrical waveguide probe inserted into an open end of a heat exchanger tube, a coupled end of the waveguide probe being located a distance from the open end by at least the distance from the open end to a heat exchanger tube sheet, means for applying an electronic transmit pulse to a magnetostrictive sensor mounted on the waveguide probe, means for generating and transmitting a torsional wave pulse in the waveguide probe by the magnetostrictive sensor, means for coupling the transmitted torsional waves from the waveguide probe to an inside wall of the heat exchanger tube for propagation along the length of the heat exchanger tube, means for coupling reflected torsional wave signals from defects and a far end of the heat exchanger tube to the waveguide probe, means for sensing the reflected torsional wave signals by a magnetostrictive sensor, and means for electronically processing the sensed signals for determining a location and characteristics of the defects in the heat exchanger tube walls. The means for applying an electronic transmit pulse may comprise a control processor for activating a function generator to produce an output pulse, a power amplifier for amplifying the output pulse to provide an electronic transmit pulse and the electronic transmit pulse being connected to the magnetostrictive sensor. The means for generating a torsional wave pulse and the means for sensing the reflected torsional wave signals may be performed by the same magnetostrictive sensor including an integrated magnetostrictive transmitter and receiver. The means for generating a torsional wave pulse and the means for sensing the reflected torsional wave signals may be performed by separate magnetostrictive sensors including a magnetostrictive transmitter and separate magnetostrictive receiver. The means for generating torsional waves may comprise means for applying an electric current pulse of a fixed frequency to a coil wound over a ferromagnetic strip of the magnetostrictive sensor cylindrically affixed on the cylindrical waveguide probe. The ferromagnetic strip may be selected from the group consisting of a nickel strip and a strip of material having good magnetostrictive properties. The system may further comprise means for magnetically polarizing the ferromagnetic strip in a circumferential direction. The means for coupling the torsional waves between the waveguide tube and the heat exchanger tube may comprise expanding the coupled end of the waveguide tube to make intimate contact between the coupled end and the inside diameter of the heat exchanger tube by applying a force from inside the waveguide tube using an expansible device. The means for coupling the torsional waves between the waveguide tube and the heat exchanger tube may comprise a drawbar mechanism being repositioned for actuating an expanding collet on the coupled end of the waveguide probe, the actuated expanding collet for expanding the coupled end of the waveguide probe to create a firm mechanical contact with the inside wall of the heat exchanger tube, the generated transmitted torsional wave being propagated from the magnetostrictive sensor to the coupled end of the waveguide probe, and the propagated torsional wave being coupled from the coupled end of the waveguide probe to the inside wall of the heat exchanger tube. The means for coupling reflected torsional wave signals may comprise the reflected torsional wave signals being coupled from the inside wall of the heat exchanger tube to the coupled end of the waveguide probe, and the reflected torsional wave signals being propagated from the coupled end of the waveguide probe to the magnetostrictive sensor. The system wherein the means for applying an electronic transmit pulse may comprise a function generator being activated by an output of a control processor for generating a transmit pulse, the transmit pulse at an output of the function generator being connected to a power amplifier input for amplifying the transmit pulse, and the amplified output pulse from an output of the power amplifier being applied to the magnetostrictive sensor, wherein the means for electronically processing the reflected torsional waves may comprise a signal from the magnetostrictive sensor being amplified in a preamplifier, the amplified signal at an output of the preamplifier being connected to an input of an analog-to-digital converter, and an output of the analog-to-digital converter being connected to an input of the control processor, and may further comprise locations and characteristics of defects in the heat exchanger tube walls being determined by the control processor using signal characteristics from the analog-to-digital converter output and the time differences between applying the electronic transmit pulse and sensing the signal characteristics from the analog-to-digital converter output.

Yet another embodiment of the present invention is a method for inspection of heat exchanger tubes using reflected torsional waves, comprising generating, transmitting and coupling a torsional wave pulse to an inside wall of a heat exchanger tube for propagation along the length of the heat exchanger tube, coupling and sensing reflected torsional wave signals from defects and a far end of the heat exchanger tube, and electronically processing the transmitted and sensed torsional waves for determining defect location and characteristics.

BRIEF DESCRIPTION OF THE DRAWINGS

These and other features, aspects and advantages of the present invention will become better understood with regard to the following description, appended claims, and accompanying drawings wherein:

DETAILED DESCRIPTION

Figure 1:
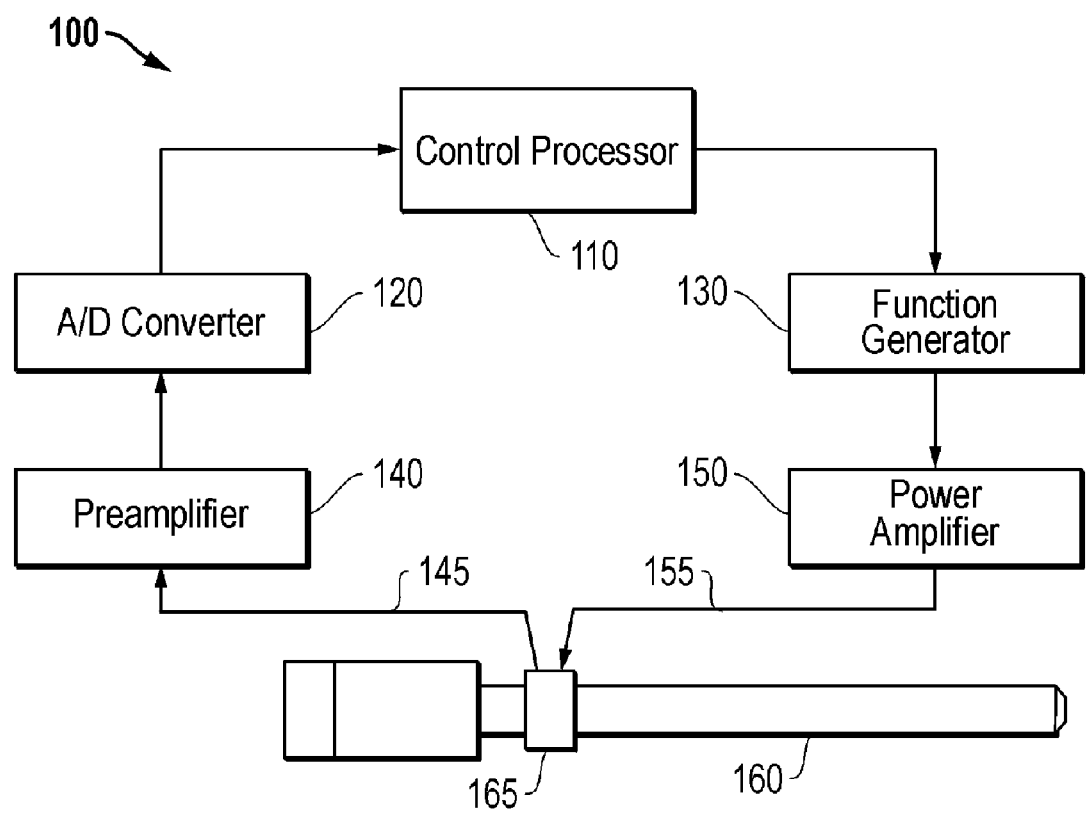
FIG. 1 shows a functional block diagram of a system for implementing the present invention.

Turning to FIG. 1, FIG. 1 shows a functional block diagram of a system 100 for implementing the present invention. A control processor 110 commands a function generator 130 to initiate an electric current pulse of a fixed frequency that is amplified by a power amplifier 150. The amplified electric current pulse 155 is sent to a magnetostrictive sensor 165 positioned on a probe 160. The amplified electric current pulse 155 causes the magnetostrictive sensor 165 to generate and transmit a torsional wave pulse into the probe waveguide tube that is coupled to a heat exchanger tube. When the torsional wave encounters a defect in the wall of the heat exchanger tube, a reflected torsional wave signal is returned to the waveguide tube coupled to the heat exchanger tube. The reflected signal produces an electrical voltage signal in the magnetostrictive sensor 165 that is amplified by a preamplifier 140. The amplified signal is then converted to a digital signal using an analog-to-digital converter 120 and sent to the control processor 110 for analysis and interpretation.

Figure 2A:
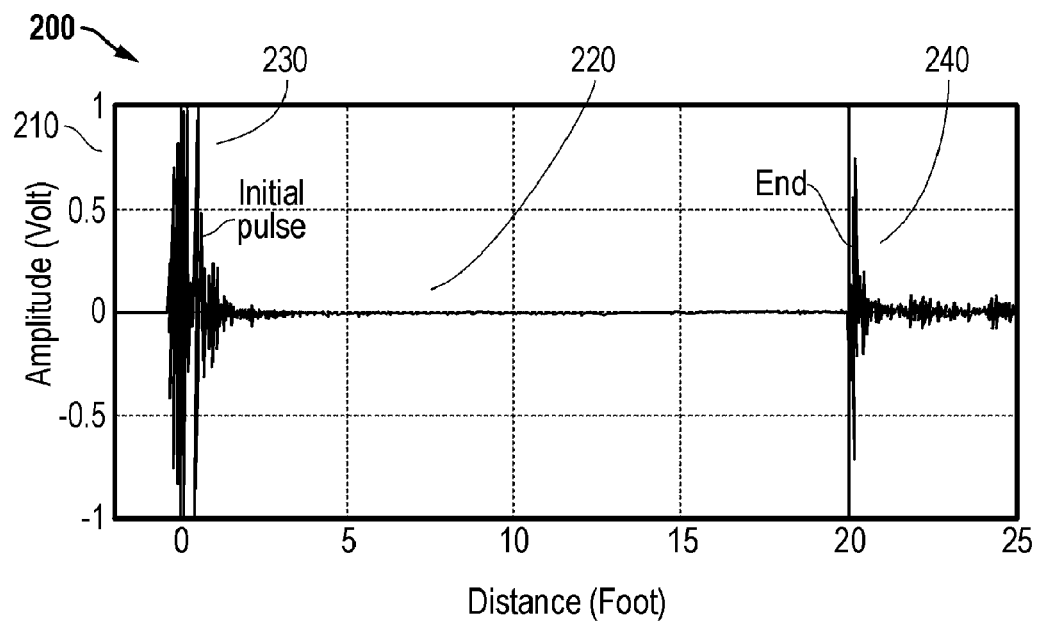
FIG. 2 shows typical representations of a transmitted torsional mode guided-wave signal and a reflected torsional mode guided-wave signal from a defect in a wall of a heat exchanger tube.
Figure 2B:
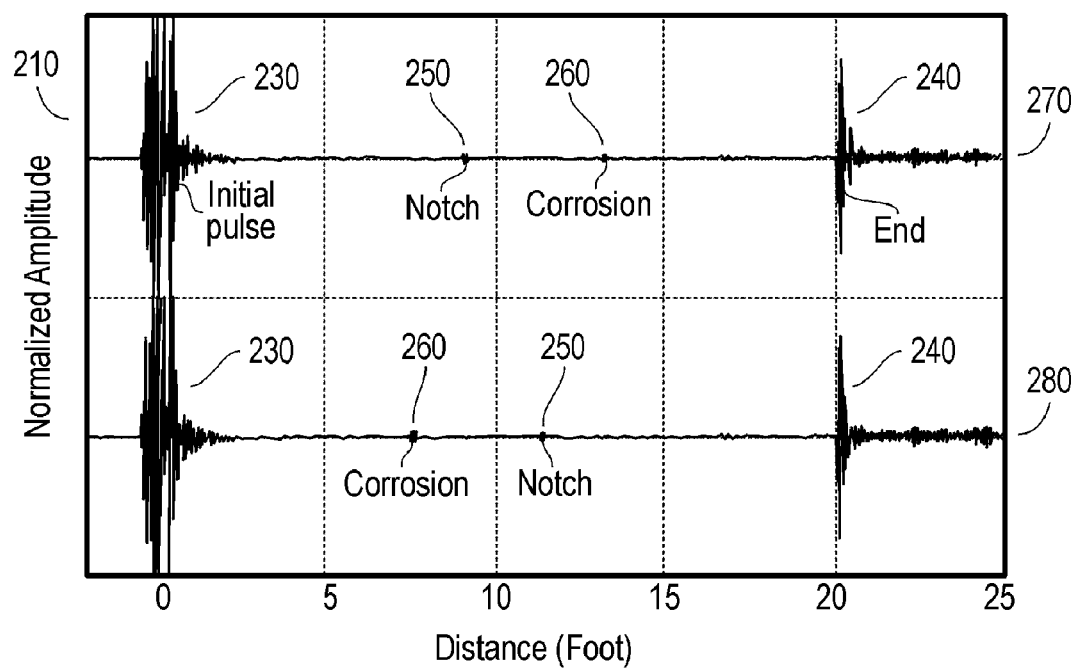

Turning to FIGS. 2A and 2B, FIG. 2A shows a typical representation 200 of a transmitted torsional mode guided-wave signal 230 and a reflected torsional mode guided-wave signal 240 from an end of a heat exchanger tube. The signals 230, 240 are represented in amplitude 210 and distance 220, as measured by a magnetostrictive sensor 165. As shown in FIG. 2, the incident wave 230 is transmitted into a heat exchanger tube, and after a time determined by a round-trip excursion between transmission of the incident signal 230 and receipt of the reflected defect signal 240 by the magnetostrictive sensor 165. The magnetostrictive sensor 165 is positioned on a suitable probe, as shown in FIG. 1. FIG. 2B also show the transmitted pulse 230 and returned pulse from an opposite end of a heat exchanger tube. In the top trace 270, reflections from a notch 250 and corrosion 260 are indicated. In the bottom trace 280, the heat exchanger tube is tested from the opposite end, showing corrosion 260 and a notch 250.

Figure 3:
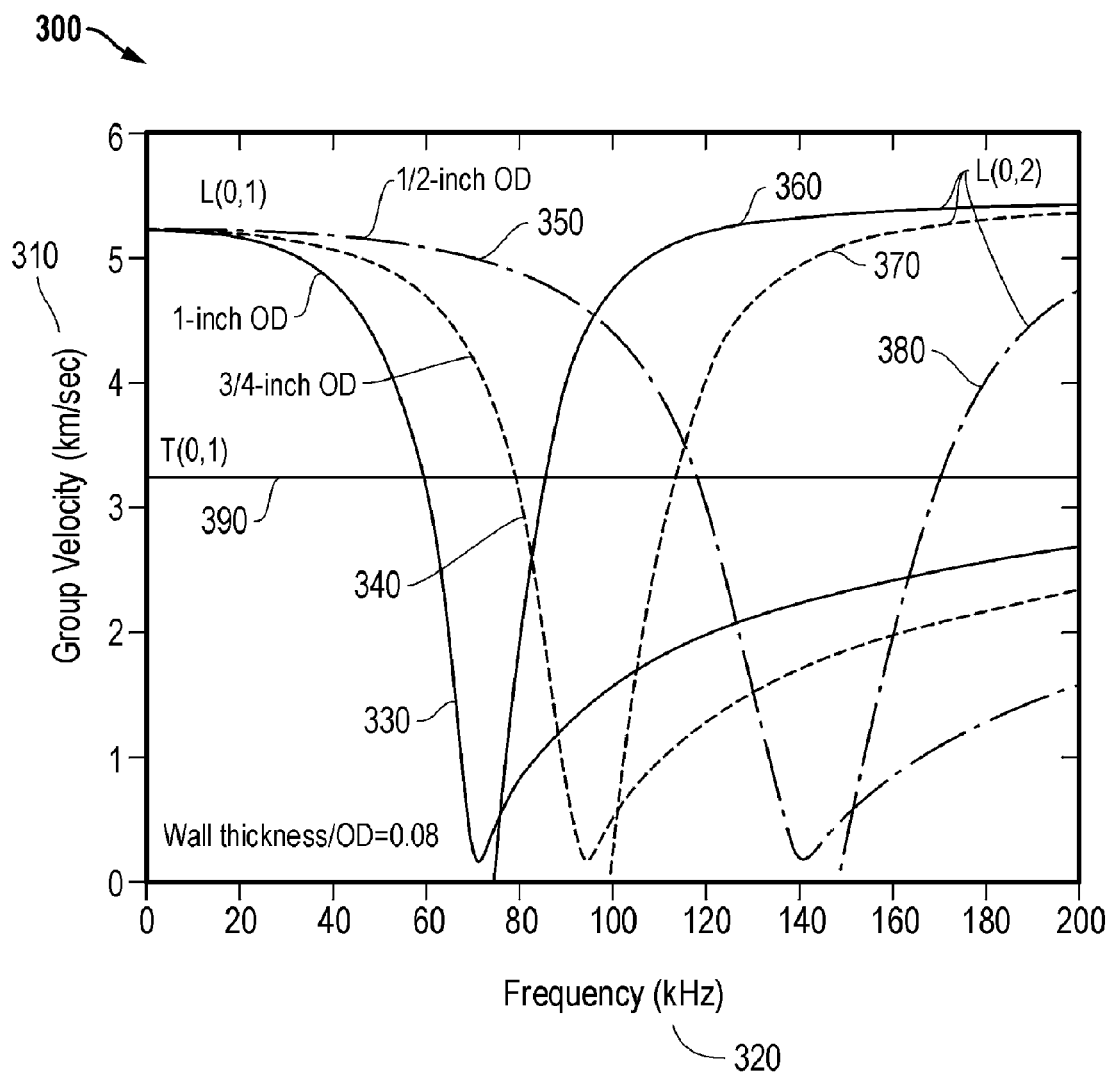
FIG. 3 shows dispersion curves for longitudinal mode and torsional mode waves in different diameter tubes.

Turning to FIG. 3, FIG. 3 shows dispersion curves 300 for longitudinal mode and torsional mode waves in different diameter tubes. This FIG. 3 illustrates the advantage of the use of torsional waves over the use of longitudinal waves for defect detection. FIG. 3 depicts how the group velocity 310 of various longitudinal waves and torsional waves changes with frequency 320 for different size tubes. The velocity of longitudinal wave mode L(0,1) for tubes of ½ inch outside diameter 350, ¾ inch outside diameter 340 and 1 inch outside diameter 330, varies between approximately zero and more than five kilometers per second over the frequency range shown. The velocity of longitudinal wave mode L(0,2) for tubes of ½ inch outside diameter 380, ¾ inch outside diameter 370 and 1 inch outside diameter 360, also varies between zero and more than five kilometers per second over the frequency range shown. In comparison to the wide variation in the longitudinal wave velocities, torsional wave mode T(0,1) for the three tube sizes 390, shows no variation in group velocity 310 independent of frequency 320.

Figure 4A:
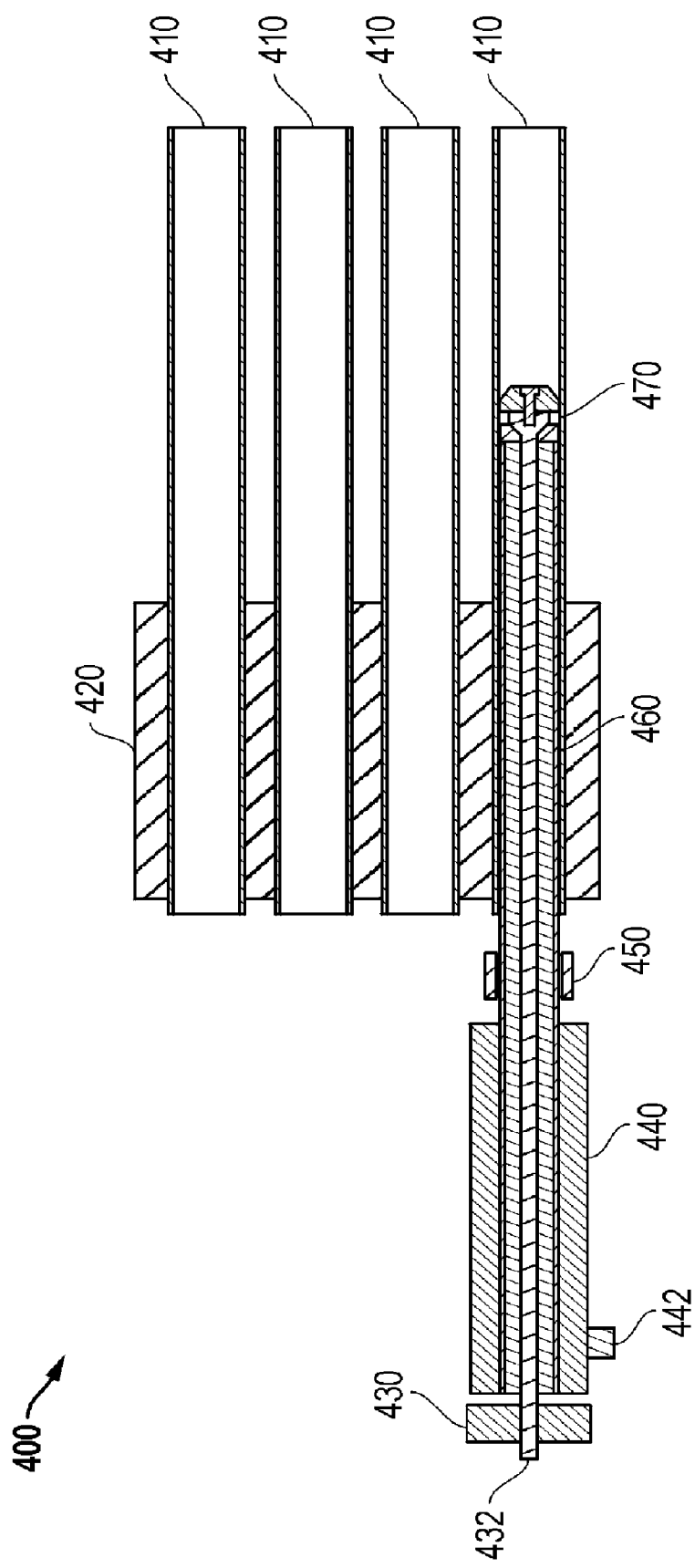
FIG. 4 shows embodiments of a torsional mode guided-wave probe.
Figure 4B:
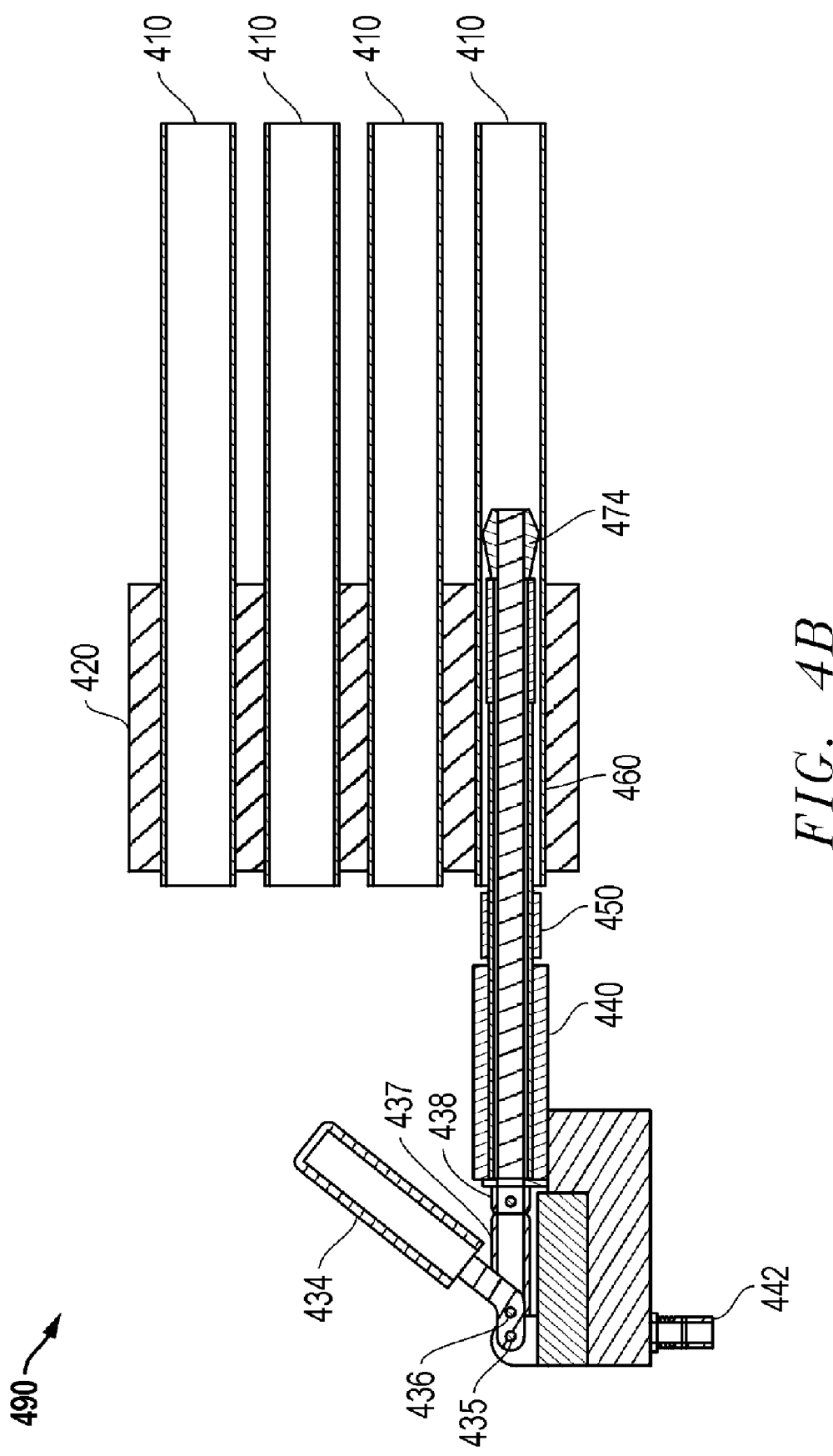

Turning to FIGS. 4A and 4B, FIG. 4A shows an embodiment of a torsional mode guided-wave probe 400 inserted into one of many heat exchanger tubes 410, positioned by a tube sheet 420. The probe 400 is similar to the probe disclosed in U.S. Pat. No. 5,892,162 having a patent date of Apr. 6, 1999, which is incorporated herein by reference. The patent discloses a guided-wave probe for inspection of tubes and pipes from the inside diameter, which relies on longitudinal guided waves that are generated in the probe's waveguide from an area outside of a heat exchanger tube. In contrast with the previously patented invention, the present invention relies on torsional wave signals for defect detection rather than longitudinal wave signals, because the torsional wave signals are much less dispersive than the longitudinal wave signals and have a velocity that is independent of tube size and wave frequency, as described above. The torsional mode signals are easier to control and have better defect detection capability than the longitudinal mode signals. The sensors used in the patented invention is different from the sensors used in the present invention. In the present invention, waves generated by a sensor 450 are propagated along the probe's waveguide 460, and mechanically coupled to the inside wall of a tube 410 at the working tip area of the probes waveguide by an expanding collet 470. The coupled area of the probe's waveguide 460 is split along its length near the collet 470, so that when tightened, the collet 470 causes the split end to expand to be in close proximity with the tube inside wall for coupling signals between the waveguide 460 and the tube 410. The present invention discloses the use of a collet 470 for expanding the working tip area of the probe 400 when a collet nut 430 is tightened down on a threaded end of a collet draw bar 435 that is rotationally connected to the expanding collet 470. The probe 400 also includes a damping material 440 positioned on the waveguide tube 460 to minimize reverberations of the guided-wave signals in the waveguide tube 460.

According to FIG. 4A, the present invention uses a sensor 450 for transmitting and detecting torsional mode signals that relies on a magnetostrictive sensor approach similar to the magnetostrictive sensor disclosed in U.S. Pat. No. 5,581, 037 having a patent date of Dec. 3, 1996, which is incorporated herein by reference. The patent discloses a magnetostrictive sensor for inspecting tubes from an inside diameter that is applicable to ferrous tubes, and uses longitudinal waves generated directly in the tube walls. The magnetostrictive sensor 450 of the present invention generates and detects torsional mode signals in the probe's waveguide 460 utilizing a thin ferromagnetic strip, similar to the magnetostrictive sensor disclosed in U.S. Pat. No. 6,396, 262 having a patent date of May 28, 2002, which is incorporated herein by reference.

As shown in FIG. 4A, to conduct an inspection of a heat exchanger tube 410, the probe 400 is inserted into an open end of the heat exchanger tube 410 such that the coupled region 470 of the probe 400 is at or just beyond the tube sheet 420. The probe 400 is then coupled to the heat exchanger tube 410 inside surface by tightening the collet nut 430, repositioning the drawbar mechanism 432. The magnetostrictive sensor 450 is then activated and torsional waves are coupled from the tip 470 of the probe 400 to the heat exchanger tube 410. The reflected signals from tube defects are returned to the sensor 450 and acquired by the associated instrumentation shown in FIG. 1. An electrical connector 442 is shown on the barrel 442 of the probe 400 for connecting the sensor signals to associated instrumentation.

FIG. 4B illustrates another embodiment 490 of the present invention. To conduct an inspection of a heat exchanger tube 410, the probe 490 is inserted into an open end of the heat exchanger tube 410 such that the coupled region 474 of the probe 400 is at or just beyond the tube sheet 420. The probe 400 is then coupled to the heat exchanger tube 410 inside surface by pulling the handle 434 such that the handle 434 pivots about a pivot point 435, causing drawbar mechanism 438, connected to a connecting rod 437 connected to the handle 434, to reposition. The repositioning action of the drawbar mechanism 438 causes the coupled region of the probe 474 to be tightened against the inside wall of the heat exchanger tube 410. The magnetostrictive sensor 450 is then activated and torsional waves are coupled from the tip 474 of the probe 400 to the heat exchanger tube 410. The reflected signals from tube defects are returned to the sensor 450 and acquired by the associated instrumentation shown in FIG. 1. An electrical connector 442 is shown on the barrel 440 of the probe 400 for connecting the sensor signals to associated instrumentation.

Figure 5:
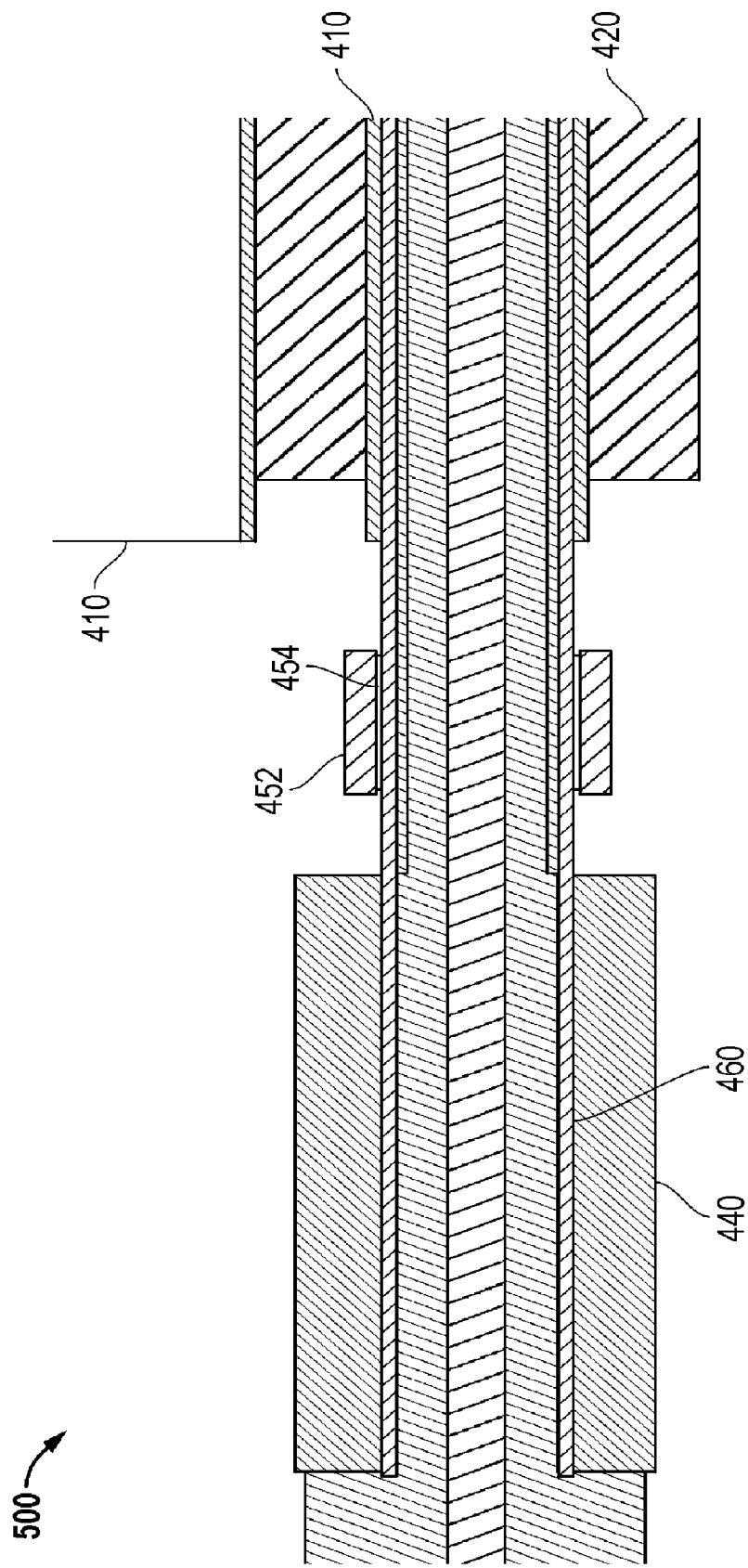
FIG. 5 shows an enlarged sensor configuration of an embodiment of a torsional mode guided-wave probe.

Turning to FIG. 5, FIG. 5 shows an enlarged sensor configuration 500 of an embodiment of a torsional mode guided-wave probe 400. FIG. 5 depicts a portion of the probe 400 shown in FIG. 4. The probe 400 is positioned in one of many heat exchanger tubes 410 fixed in position by a tube sheet 420. A sensor 450 comprises a sensor coil 452 and a cylindrical ferromagnetic strip 454, such as nickel or other material with suitable magnetostrictive properties, that is securely affixed to an outside wall of the waveguide tube 460 for providing magnetostrictive properties necessary for the generation and detection of torsional wave signals according to the present invention. A time-varying magnetic field generated by the sensor coil 452 generates torsional waves in the cylindrical ferromagnetic strip 454 via the magnetostrictive effect. The cylindrical ferromagnetic strip 454 and the sensor coil 452 are also used to detect reflected waves from a tube defect via the inverse magnetostrictive effect. The damping material 440 is also shown positioned on the waveguide tube 460 to minimize reverberations of the guided-wave signals in the waveguide tube 460.

For generation and detection of torsional mode signals, a DC bias magnetic field is required in the circumferential direction. Bias magnetization in a circumferential direction may be accomplished by inducing residual magnetization in the ferromagnetic strip 454 along its length prior to circumferentially attaching or wrapping the strip 454 to the waveguide tube 460. Another method for creating a circumferential bias magnetic field in the ferromagnetic strip 454 is, after attaching the strip to the waveguide tube, to pass a DC electric along the longitudinal axis of the guided wave probe tube 460. The electric current flow is in a direction of a longitudinal axis of the waveguide tube 460.

Figure 6A:
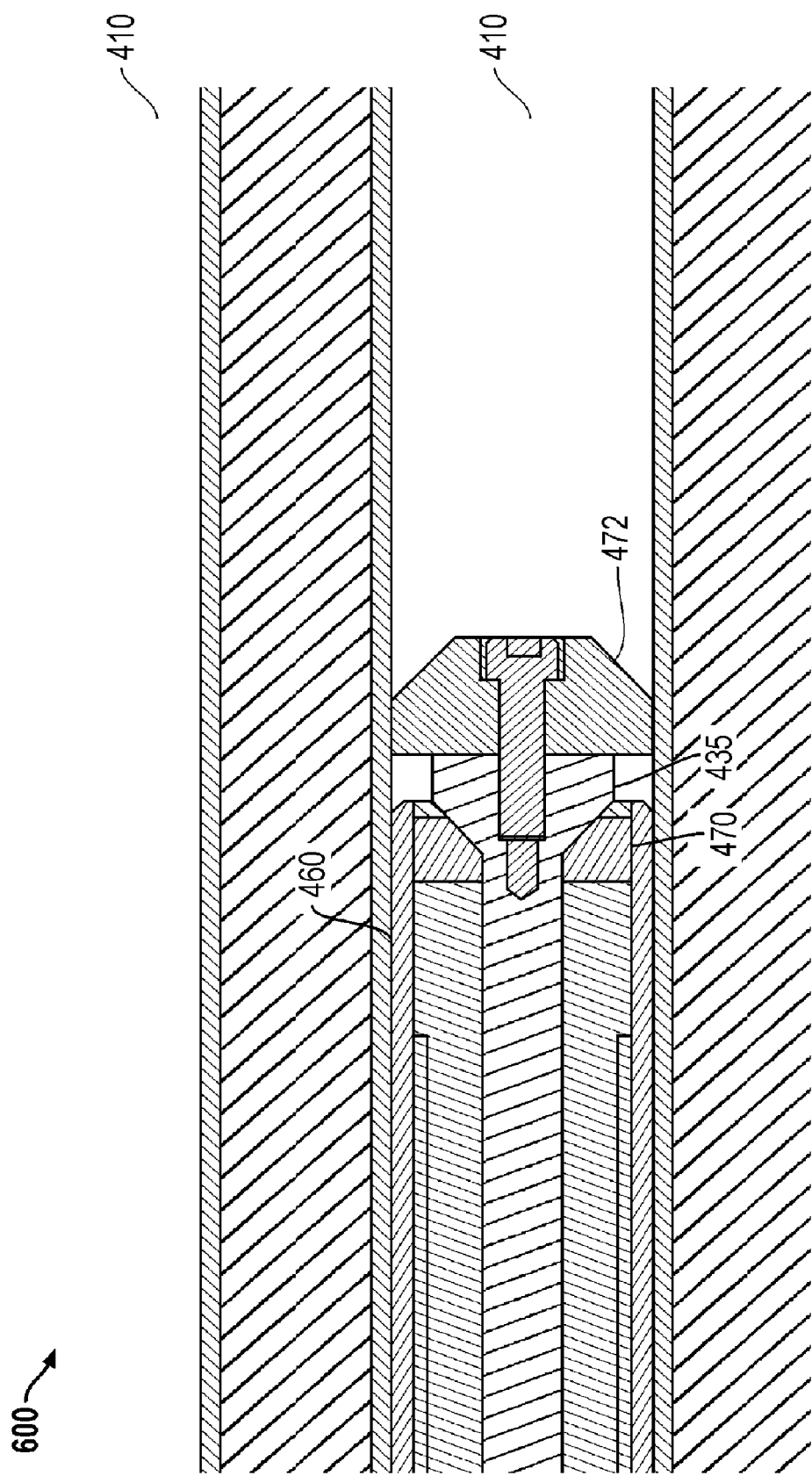
FIG. 6 shows enlarged waveguide tip configurations as embodiments of a torsional mode guided-wave probe.
Figure 6B:
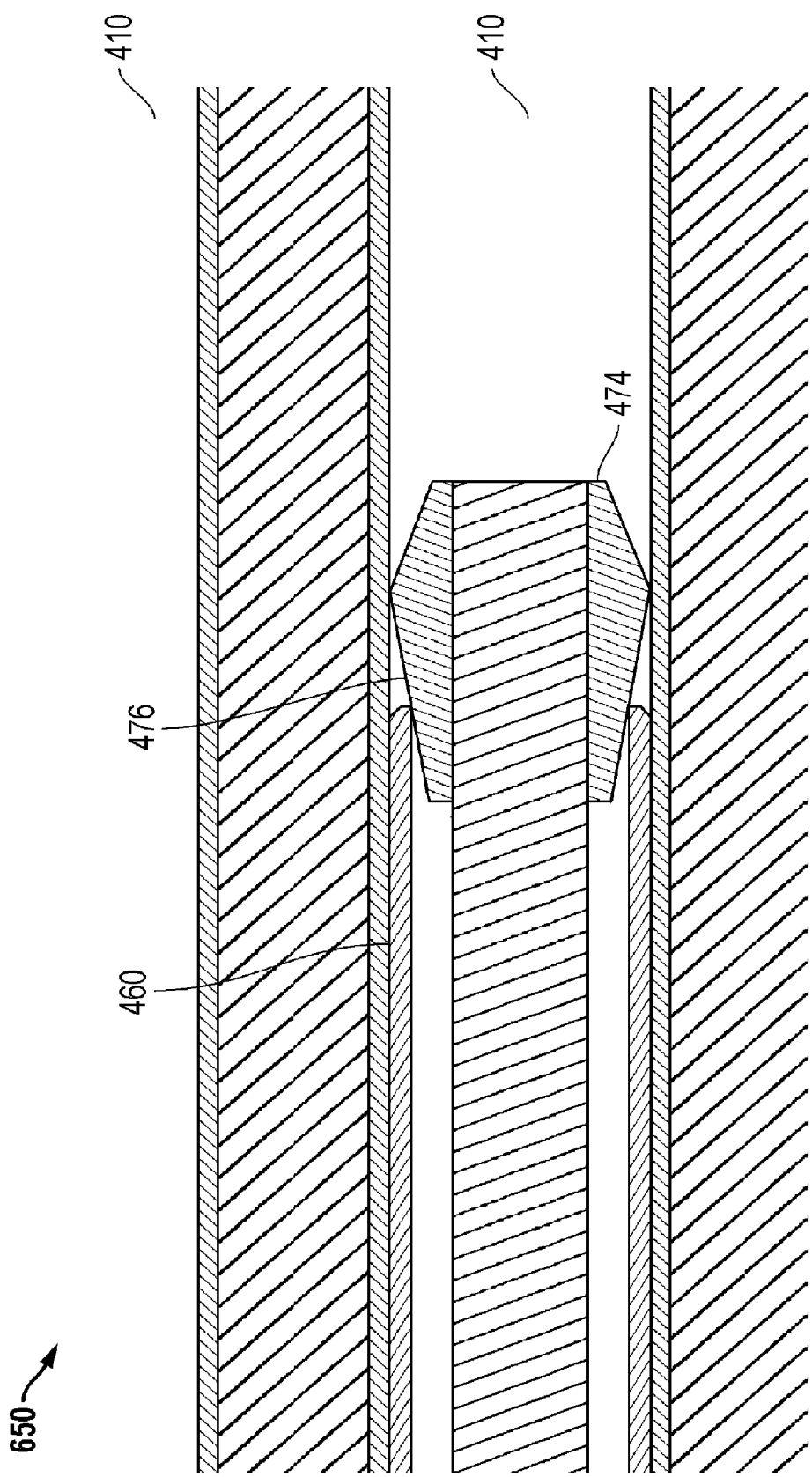

Turning to FIGS. 6A and 6B, FIG. 6A shows an enlarged waveguide working tip configuration 600 of an embodiment of a torsional mode guided-wave probe 400. The tip of the waveguide tube 460 contains axial slits positioned around the tube circumference in the region near the working tip of the waveguide tube 460. Torsional waves generated in the waveguide tube 460 are mechanically coupled to a heat exchanger tube 410 using a collet drawbar mechanism 435. FIG. 6A shows how the collet 470 is expanded when the nose piece 475 is forced into the collet 470 by the drawbar 435 when a user tightens the drawbar nut 430 to reposition the drawbar 435, mechanically coupling the waveguide tube tip 460 to the inside of the heat exchanger tube 410.

Similarly, FIG. 6B shows another embodiment of an enlarged waveguide working tip configuration 650 of a torsional guided wave probe. The tip of the waveguide tube 460 contains axial slits positioned around the tube circumference in the region near the working tip of the waveguide tube 460. Torsional waves generated in the waveguide tube 460 are mechanically coupled to a heat exchanger tube 410 using a drawbar mechanism 474. FIG. 6B shows how the drawbar nose piece 476 causes the tip of the waveguide tube 460 to be expanded when the nose piece 476 is forced into the tip of the waveguide tube 460 when a user repositions the drawbar 474, mechanically coupling the waveguide tube tip 460 to the inside of the heat exchanger tube 410.

Figure 7A:
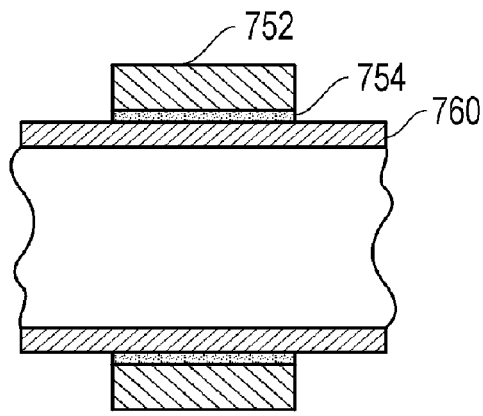
FIG. 7 shows details of a magnetostrictive sensor for generating and detecting torsional mode guided wave signals.
Figure 7B:
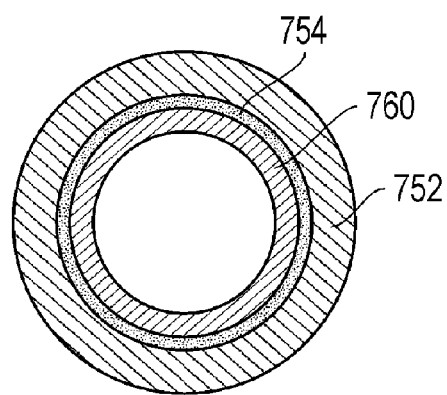

Turning to FIG. 7, FIG. 7 shows details of a magnetostrictive sensor for generating and detecting torsional mode guided wave signals. FIGS. 7A and 7B illustrate a more detailed view of the magnetostrictive sensor (450 shown in FIGS. 4 and 5). FIGS. 7A and 7B show a cylindrical ferromagnetic strip 754 affixed to the waveguide tube 760. The sensor coil 752 is wound over the cylindrical ferromagnetic strip 754 that contains bias residual magnetization. The ferromagnetic strip 754 is typically an inch wide and wrapped around the waveguide tube 760. The width of the ferromagnetic strip 754 may be adjusted according to the frequency of the guided waves, being narrower for high frequencies and wider for lower frequencies. The ferromagnetic strip 754 may be made from any material that has good magnetostrictive characteristics, such as nickel, grain-oriented silicon steel, or other magnetostrictive material that has the ability to retain residual magnetism and a high magnetostrictive coefficient. The residual magnetic field is induced in the ferromagnetic strip 754 by applying a suitable energizing magnetic field to the ferromagnetic strip 754 and removing the energizing magnetic field such that the direction of the induced magnetic field is circumferential when cylindrical ferromagnetic strip 754 is wrapped around the waveguide tube. After affixing the cylindrical ferromagnetic strip 754 to the waveguide tube 760, the magnetostrictive sensor coil 752 is placed around the cylindrical ferromagnetic strip 754. For generation of torsional mode waves, the DC bias magnetic field must be in a circumferential direction around the waveguide tube 760 as described. In contrast, for generation of longitudinal mode waves, the DC bias magnetic field must be in a longitudinal or lengthwise direction of the waveguide tube 760.

Figure 7C:
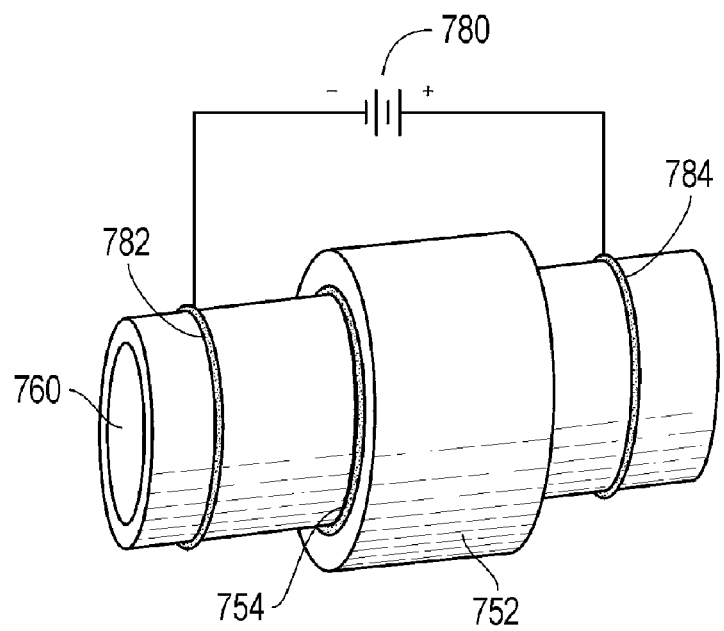

Another method of creating a circumferential bias magnetic field in the cylindrical ferromagnetic strip 754 is illustrated in FIG. 7C. As shown in FIG. 7C, a DC current is caused to be passed between conductive rings 782, 784 around an electrically conductive waveguide tube 760. This current causes a circumferential magnetic field to be induced in the cylindrical ferromagnetic strip 754. If the waveguide tube 760 is not electrically conductive, a heavy gauge copper wire may be inserted through the waveguide tube and a DC current applied to the copper wire to achieve the same result.

Although the present invention has been described in detail with reference to certain preferred embodiments, it should be apparent that modifications and adaptations to those embodiments might occur to persons skilled in the art without departing from the spirit and scope of the present invention.

What is claimed is:

1. A method for inspection of heat exchanger tubes using reflected torsional waves, comprising the steps of:
    inserting a cylindrical waveguide probe into an open end of a heat exchanger tube, a coupled end of the waveguide probe being located a distance from the open end by at least the distance from the open end to a heat exchanger tube sheet;
    applying an electronic transmit pulse to a magnetostrictive sensor mounted on the waveguide probe;
    generating and transmitting a torsional wave pulse in the waveguide probe by the magnetostrictive sensor;
    coupling the transmitted torsional wave from the waveguide probe to an inside wall of the heat exchanger tube for propagation along the length of the heat exchanger tube;
    coupling reflected torsional wave signals from defects and a far end of the heat exchanger tube to the waveguide probe;
    sensing the reflected torsional wave signals by a magnetostrictive sensor; and
    electronically processing the sensed signals for determining a location and characteristics of the defects in the heat exchanger tube walls.

2. The method of claim 1, wherein the step of generating a torsional wave pulse and the step of sensing the reflected torsional wave signals are performed by the same magnetostrictive sensor including an integrated magnetostrictive transmitter and receiver.

3. The method of claim 1, wherein the step of generating a torsional wave pulse and the step of sensing the reflected torsional wave signals are performed by separate magnetostrictive sensors including a magnetostrictive transmitter and separate magnetostrictive receiver.

4. The method of claim 1, wherein the step of generating torsional waves comprises applying an electric current pulse of a fixed frequency to a coil wound over a ferromagnetic strip of the magnetostrictive sensor cylindrically affixed on the cylindrical waveguide probe.

5. The method of claim 4, wherein the ferromagnetic strip is selected from the group consisting of a nickel strip and a strip of material having good magnetostrictive properties.

6. The method of claim 4, further comprising the step of magnetically polarizing the ferromagnetic strip in a circumferential direction.

7. The method of claim 1, wherein the step of coupling the torsional waves between the waveguide tube and the heat exchanger tube comprises expanding the coupled end of the waveguide tube to make intimate contact between the coupled end and the inside diameter of the heat exchanger tube by applying a force from inside the waveguide tube using an expansible device.

8. The method of claim 1:
    wherein the step of applying an electronic transmit pulse comprises activating a function generator by an output of a control processor for generating a transmit pulse, connecting the transmit pulse at an output of the function generator to a power amplifier input for amplifying the transmit pulse, and applying the amplified output pulse from the output of the power amplifier to the magnetostrictive sensor;
    wherein the step of electronically processing the reflected torsional waves comprises amplifying a signal from the magnetostrictive sensor in a preamplifier, connecting the amplified signal at an output of the preamplifier to an input of an analog-to-digital converter, and connecting an output of the analog-to-digital converter to an input of the control processor; and
    further comprising the step of determining locations and characteristics of defects in the heat exchanger tube walls by the control processor using signal characteristics from the analog-to-digital converter output and the time differences between applying the electronic transmit pulse and sensing of the signal characteristics from the analog-to-digital converter output.

9. A system for inspection of heat exchanger tubes using reflected torsional waves, comprising:
    a cylindrical waveguide probe inserted into an open end of a heat exchanger tube, a coupled end of the waveguide probe being located a distance from the open end by at least the distance from the open end to a heat exchanger tube sheet;
    means for applying an electronic transmit pulse to a magnetostrictive sensor mounted on the waveguide probe;
    means for generating and transmitting a torsional wave pulse in the waveguide probe by the magnetostrictive sensor;
    means for coupling the transmitted torsional waves from the waveguide probe to an inside wall of the heat exchanger tube for propagation along the length of the heat exchanger tube;
    means for coupling reflected torsional wave signals from defects and a far end of the heat exchanger tube to the waveguide probe;
    means for sensing the reflected torsional wave signals by a magnetostrictive sensor; and
    means for electronically processing the sensed signals for determining a location and characteristics of the defects in the heat exchanger tube walls.

10. The system of claim 9, wherein the means for applying an electronic transmit pulse comprises:
    a control processor for activating a function generator to produce an output pulse;
    a power amplifier for amplifying the output pulse to provide an electronic transmit pulse; and
    the electronic transmit pulse being connected to the magnetostrictive sensor.

11. The system of claim 9, wherein the means for generating a torsional wave pulse and the means for sensing the reflected torsional wave signals are performed by the same magnetostrictive sensor including an integrated magnetostrictive transmitter and receiver.

12. The system of claim 9, wherein the means for generating a torsional wave pulse and the means for sensing the reflected torsional wave signals are performed by separate magnetostrictive sensors including a magnetostrictive transmitter and separate magnetostrictive receiver.

13. The method of claim 9, wherein the means for generating torsional waves comprises means for applying an electric current pulse of a fixed frequency to a coil wound over a ferromagnetic strip of the magnetostrictive sensor cylindrically affixed on the cylindrical waveguide probe.

14. The system of claim 13, wherein the ferromagnetic strip is selected from the group consisting of a nickel strip and a strip of material having good magnetostrictive properties.

15. The system of claim 13, further comprising means for magnetically polarizing the ferromagnetic strip in a circumferential direction.

16. The system of claim 9, wherein the means for coupling the torsional waves between the waveguide tube and the heat exchanger tube comprises expanding the coupled end of the waveguide tube to make intimate contact between the coupled end and the inside diameter of the heat exchanger tube by applying a force from inside the waveguide tube using an expansible device.

17. The system of claim 9, wherein the means for coupling the torsional waves between the waveguide tube and the heat exchanger tube comprises:

a drawbar mechanism being repositioned for actuating an expanding collet on the coupled end of the waveguide probe, the actuated expanding collet for expanding the coupled end of the waveguide probe to create a firm mechanical contact with the inside wall of the heat exchanger tube;

the generated transmitted torsional wave being propagated from the magnetostrictive sensor to the coupled end of the waveguide probe; and the propagated torsional wave being coupled from the coupled end of the waveguide probe to the inside wall of the heat exchanger tube.

18. The system of claim 17, wherein the means for coupling reflected torsional wave signals comprises:

the reflected torsional wave signals being coupled from the inside wall of the heat exchanger tube to the coupled end of the waveguide probe; and the reflected torsional wave signals being propagated from the coupled end of the waveguide probe to the magnetostrictive sensor.

19. The system of claim 9:

wherein the means for applying an electronic transmit pulse comprises a function generator being activated by an output of a control processor for generating a transmit pulse, the transmit pulse at an output of the function generator being connected to a power amplifier input for amplifying the transmit pulse, and the amplified output pulse from an output of the power amplifier being applied to the magnetostrictive sensor;

wherein the means for electronically processing the reflected torsional waves comprises a signal from the magnetostrictive sensor being amplified in a preamplifier, the amplified signal at an output of the preamplifier being connected to an input of an analog-to-digital converter, and an output of the analog-to-digital converter being connected to an input of the control processor; and further comprising locations and characteristics of defects in the heat exchanger tube walls being determined by the control processor using signal characteristics from the analog-to-digital converter output and the time differences between applying the electronic transmit pulse and sensing the signal characteristics from the analog-to-digital converter output.

20. A method for inspection of heat exchanger tubes using reflected torsional waves, comprising:

generating, transmitting and coupling a torsional wave pulse to an inside wall of a heat exchanger tube for propagation along the length of the heat exchanger tube;

coupling and sensing reflected torsional wave signals from defects and a far end of the heat exchanger tube; and electronically processing the transmitted and sensed torsional waves for determining defect location and characteristics.

* * * * *